(12) United States Patent
Linder et al.

(10) Patent No.: US 10,124,094 B2
(45) Date of Patent: Nov. 13, 2018

(54) ADAPTIVE ALGORITHM FOR THORACIC DRAINAGE THERAPY

(75) Inventors: Albert Linder, Bremen (DE); Hilmar Ehlert, Hergiswil (CH); Martin Walti, Zurich (CH)

(73) Assignee: MEDELA HOLDING AG, Baar (CH)

( * ) Notice: Subject to any disclaimer, the term of this patent is extended or adjusted under 35 U.S.C. 154(b) by 685 days.

(21) Appl. No.: 14/122,406

(22) PCT Filed: May 24, 2012

(86) PCT No.: PCT/CH2012/000117
§ 371 (c)(1),
(2), (4) Date: Dec. 16, 2013

(87) PCT Pub. No.: WO2012/162848
PCT Pub. Date: Dec. 6, 2012

(65) Prior Publication Data
US 2014/0100540 A1 Apr. 10, 2014

(30) Foreign Application Priority Data
May 27, 2011 (CH) .......................................... 909/11

(51) Int. Cl.
*A61M 1/00* (2006.01)
*A61M 1/04* (2006.01)

(52) U.S. Cl.
CPC ........ *A61M 1/0031* (2013.01); *A61M 1/0023* (2013.01); *A61M 1/04* (2013.01);
(Continued)

(58) Field of Classification Search
CPC combination set(s) only.
See application file for complete search history.

(56) References Cited

U.S. PATENT DOCUMENTS

| 4,370,983 A * | 2/1983 | Lichtenstein ............ A61B 5/00 600/301 |
| 4,592,741 A * | 6/1986 | Vincent ............... A61M 1/0023 604/118 |

(Continued)

FOREIGN PATENT DOCUMENTS

| EP | 1894584 A2 * | 3/2008 | .......... A61M 1/0013 |
| EP | 1894584 A2 | 3/2008 | |

(Continued)

OTHER PUBLICATIONS

Parmasivam, et. al., "Air leaks, pneumothorax, and chest drains"; Continuing Education in Anaesthesia, Critical Care & Pain, vol. 8, No. 6 (2008), pp. 204-209; Oxford University Press, Oxford, UK.*

(Continued)

*Primary Examiner* — Guy K Townsend
(74) *Attorney, Agent, or Firm* — Marshall, Gerstein & Borun LLP

(57) ABSTRACT

Devices and to methods for thoracic drainage for a patient having an air fistula. A vacuum is produced in the pleural cavity of the patient by means of a suction device. In order to adjust the vacuum on the basis of objective criteria, a suitable size measure for the air fistula is determined and the vacuum produced by the suction device is controlled according to said size measure. An adaptive algorithm includes: (a) determining a first value of a size measure for the air fistula; (b) changing the vacuum by a first difference value; (c) determining a second value of the size measure after a first waiting period; (d) changing the vacuum by a second difference value having the opposite sign if the second measure is greater than the first measure; (e) repeating steps (a) to (d) after a second waiting period.

13 Claims, 3 Drawing Sheets

(52) U.S. Cl.
CPC ... *A61M 1/0088* (2013.01); *A61M 2205/3331* (2013.01); *A61M 2205/3334* (2013.01); *A61M 2205/3344* (2013.01); *A61M 2210/101* (2013.01)

(56) References Cited

U.S. PATENT DOCUMENTS

| | | | | |
|---|---|---|---|---|
| 4,654,029 | A * | 3/1987 | D'Antonio | A61M 1/0031 600/584 |
| 5,738,656 | A * | 4/1998 | Wagner | A61M 1/0084 604/119 |
| 6,352,525 | B1 * | 3/2002 | Wakabayashi | A61M 1/0023 604/19 |
| 2003/0187367 | A1 * | 10/2003 | Odland | A61M 1/0023 600/573 |
| 2004/0260255 | A1 * | 12/2004 | Charlez | A61M 1/0013 604/317 |
| 2005/0203469 | A1 * | 9/2005 | Bobroff | A61M 1/0003 604/318 |
| 2008/0200905 | A1 * | 8/2008 | Heaton | A61M 1/0011 604/543 |
| 2010/0174270 | A1 * | 7/2010 | Charlez | A61M 1/0013 604/540 |
| 2011/0015619 | A1 * | 1/2011 | Svedman | A61L 15/60 604/543 |
| 2011/0071415 | A1 * | 3/2011 | Karwoski | A61B 5/08 600/529 |
| 2011/0092958 | A1 * | 4/2011 | Jacobs | A61M 1/0031 604/543 |
| 2011/0112493 | A1 * | 5/2011 | Koch | A61M 1/0013 604/319 |
| 2014/0100540 | A1 * | 4/2014 | Linder | A61M 1/0023 604/319 |

FOREIGN PATENT DOCUMENTS

| | | |
|---|---|---|
| WO | WO-01/21129 A2 | 3/2001 |
| WO | WO-2005/061025 A1 | 7/2005 |
| WO | WO-2007/128156 A2 | 11/2007 |
| WO | WO-2009/005424 A1 | 1/2009 |
| WO | WO 2009005424 A1 * | 1/2009 .......... A61M 1/0013 |

OTHER PUBLICATIONS

Written Opinion of the International Searching Authority of International Application No. PCT/CH2012/000117, dated Aug. 27, 2012.

International Search Report of International Application No. PCT/CH2012/000117, dated Aug. 27, 2012.

International Preliminary Report on Patentability for International Application No. PCT/CH2012/000117 dated Dec. 12, 2013 (Including English Translation of Written Opinion).

\* cited by examiner

ADAPTIVE ALGORITHM FOR THORACIC DRAINAGE THERAPY

CROSS-REFERENCE TO RELATED APPLICATION

The present application is the United States national phase of International Patent Application No. PCT/CH2012/000117, filed May 24, 2012, which application claims priority of Switzerland Application No. 0909/11, filed May 27, 2011. The entire text of the priority application is incorporated herein by reference.

TECHNICAL FIELD

Field of the Disclosure

The present invention relates to an appliance for thoracic drainage and to a corresponding method and computer program.

Prior Art

In patients with defects on the lung surface, air losses in the thorax can occur which lead to the accumulation of air in the pleural space. A defect that leads to admission of air into the pleural space is generally designated below as an air fistula. Air fistulas are generally treated by thoracic drainage (pleural drainage), in which a vacuum is applied to the pleural space via a catheter leading into the pleural space.

An important parameter for the characterization of the air fistula is the quantity of air that is aspirated through the drainage system per unit of time. This volumetric flow is sometimes designated below as fistula volume. The extent of this volumetric flow changes depending on the functional size of the defect on the lung surface.

The primary goal in the treatment of patients with air fistulas is generally to minimize the length of time that the air fistula is present. Such minimization secondarily entails, in particular, a reduction in the duration of the thoracic drainage, in the risk of infection associated with the drainage, in the length of the hospital stay, and in the medical, nursing and technical labor required for treating the patient.

One parameter that can positively or negatively influence the healing process of an air fistula is the level of the vacuum applied to the pleural space. At present, however, there are no standard treatment recommendations concerning the regulation of the vacuum in thoracic drainage systems for treating air fistulas. The pressure is in most cases decided on the basis of the physician's experience and is individually and manually adjusted once or twice a day by the physician during visits to the patient's bedside.

According to U.S. Pat. No. 5,738,656, the vacuum of a thoracic drainage system is optimal when it leads to a maximum volumetric flow of the removed air. It should be noted in this connection that, with an increasing vacuum, the volumetric flow can also decrease again, the reason being that, if the vacuum is too high, there is the possibility of, e.g., peripheral lung parts or clots blocking the suction lumen. In clinical practice, however, fairly low vacuum values are in fact usually chosen. The vacuum is generally set manually by the physician, such that the lung is just expanded and the volumetric flow is as low as possible.

DISCLOSURE OF THE INVENTION

It is an object of the present invention to make available a thoracic drainage appliance that permits an improved adjustment of the vacuum, in particular an adjustment that is more objective and is specific to the patient.

In a first aspect, therefore, the present invention makes available an appliance for thoracic drainage in patients with an air fistula, said appliance comprising:
  a suction device for generating a vacuum in the pleural space; and
  a control device for controlling the suction device.

The appliance has at least one measuring device, which allows the control device to determine a parameter indicating the size of the air fistula. The control device is then configured to regulate the level of the vacuum generated by the suction device as a function of this size parameter.

Whereas in the prior art the level of the aspirating vacuum is generally fixed manually by the physician, the present invention proposes that a suitable parameter indicating the functional size of the air fistula is determined and that the aspirating vacuum is set automatically on the basis of this parameter. The term "functional size" is to be understood as the effective cross section through which air enters the pleural space. By determining a parameter indicating the functional size of the air fistula, the healing process becomes more objective, and, since this size is used to control the suction device, said suction device is controlled automatically on the basis of the objective healing process. In this way, the healing process can be better documented and, in some cases, also made significantly shorter.

In particular, the control device can be configured in such a way that, during its operation, it carries out a method having the following steps:
  (a) determining a first value of the size parameter indicating the size of the air fistula;
  (b) changing the vacuum by a first differential value;
  (c) determining a second value of the size parameter after a first waiting period;
  (d) changing the vacuum by a second differential value, which has an opposite sign compared to the first differential value, if the second value of the size parameter is greater than the first value of the size parameter;
  (e) repeating steps (a)-(d) after a second waiting period.

In particular, the control device can increase the vacuum by the first differential value in step (b) and, accordingly, lower the vacuum by the second differential value in step (d) if appropriate. In this case, the appliance therefore automatically monitors, with an adaptive algorithm, whether the air fistula is becoming functionally larger or smaller during application of the vacuum increased by the first differential value. If the parameter indicating the functional size of the air fistula has become greater, the appliance concludes from this that the chosen vacuum value was too high and reduces this value by the second differential value. Otherwise, the vacuum is left unchanged. In this way, air fistulas whose functional size becomes smaller under an increased vacuum ("closing fistulas") and air fistulas whose size becomes larger under an increased vacuum ("opening fistulas") can be automatically detected and optimally treated. Alternatively of course, in step (b), the vacuum can also firstly be lowered and, accordingly, increased in step (d) if the air fistula becomes functionally larger during application of the vacuum lowered in step (b).

In order to permit the automatic regulation, the control device preferably has a digital processor and a memory in which a computer program is stored which, when executed by the processor, causes the control device to carry out a corresponding automatic regulation.

The measuring device for determining the size parameter for the air fistula preferably comprises a suitable pressure gauge for measuring the applied vacuum, as is known per se from the prior art, and/or a suitable flow meter for measuring the volumetric flow, as is also known per se from the prior art. A thoracic drainage appliance with such a pressure gauge and with such a flow meter is available, for example, under the name THOPAZ™ from Medela AG, Baar, Switzerland. The size parameter for the air fistula is therefore determined indirectly from the pressure and/or the volumetric flow. If a flow meter is present, the latter preferably directly measures the volumetric flow passing through the suction device. However, it is also conceivable in principle for the volumetric flow to be determined indirectly, e.g. by a measurement of the pressure difference between a proximal end and a distal end of the suction lumen through which the air is aspirated from the pleural space, and the volumetric flow can be calculated from this if the flow resistance of the suction lumen is known. Such a method is described in detail in U.S. Pat. No. 5,738,656 for example.

It is conceivable in principle to determine the size parameter for the air fistula solely from measured values of the volumetric flow or solely from pressure measurements. A method that solely uses pressure measurements to determine a parameter for the size of an air fistula is proposed in US 2011/0071415 for example. In the latter document, a parameter for the size of the air fistula is determined by measuring the change of the pressure in the pleural space over time. In particular, said document proposes using the integral of the pressure over time as a parameter for the size of the air fistula.

According to a second aspect of the invention, however, both the vacuum and also the volumetric flow are taken into consideration in determining the size parameter for the air fistula. To this end, the control device preferably carries out the following steps:

using the pressure gauge to determine a measured value for the vacuum generated in the pleural space;
using the flow meter to determine a measured value for the volumetric flow through the air fistula;
calculating the size parameter from the measured values for the volumetric flow and the vacuum.

In this case, the control device thus mathematically links the measured values of the volumetric flow and of the vacuum to each other, in order thereby to allow a conclusion regarding the functional size of the air fistula. This permits a more exact determination of the size of the air fistula than is possible with methods using solely the pressure or the volumetric flow. This is based on the finding that, with a constant fistula size, a higher vacuum also leads to a higher volumetric flow. By linking the volumetric flow and the vacuum to each other, it is possible to take this relationship into account. In this way, it is possible to calculate a fistula size parameter that is less dependent on the applied vacuum than, for example, the volumetric flow alone.

Such a determination of a parameter for the size of the air fistula is advantageous even independently of an automatic regulation of the vacuum. Thus, for example, the appliance can have a display device in order to visually present the parameter for the size of the air fistula as a diagnostic parameter (as numbers and/or in graph form). Alternatively or additionally, the appliance can have a memory in order to store the parameter for the size of the air fistula. The appliance can also have an interface in order to read out the parameter for the size of the air fistula. Each of these measures gives the medical personnel in charge of the treatment a more objective view of the course of treatment than is the case in the prior art.

It is in particular preferable to calculate the size parameter in such a way that the result is at least approximately independent of the vacuum applied. To this end, the control device is preferably configured to calculate the size parameter for the air fistula by forming a variable which is substantially a function of the quotient from the measured value for the volumetric flow and the square root of the measured value for the vacuum. This is based on the finding that the quotient of the volumetric flow over the root of the vacuum pressure is generally directly proportional to the cross-sectional size of the air fistula.

In particular, the size parameter can be calculated as follows:

$$F = c\log_n\left(\frac{Q}{\sqrt{p}}\right),$$

where
 F is the size parameter for the air fistula,
 Q is the measured value for the volumetric flow,
 p is the measured value for the vacuum,
 c is a constant, preferably c=1, and
 n is a positive real number, preferably n=5.

In this way, a dimensionless indicator F is made available which permits a very simple estimation of the fistula size.

The term "vacuum" is always to be understood in this document as a negative pressure difference in relation to the atmospheric pressure. The expression "increasing the vacuum" is to be understood as meaning that the absolute value of this negative pressure difference is increased. The expression "lowering the vacuum" is to be understood as meaning that the absolute value of the negative pressure difference is reduced. All the figures given for pressure values relate herein below to the respective absolute values.

Customary values for the initially applied vacuum are generally approximately 10-50 mbar (1-5 kPa), although it is also possible in some cases to depart from this range. The first differential value by which the vacuum is in each case increased or lowered in step (b) of the proposed method is preferably between 2 and 10 mbar, particularly preferably between 4 and 6 mbar, and can in particular be approximately 5 mbar. The second differential value is preferably greater than the first differential value, preferably greater than the first differential value by a factor of between 1.5 and 3, and can in particular be approximately twice as great as the first differential value. In other words, the vacuum in step (d) is preferably lowered to a value that is lower than the value that prevailed before the vacuum in step (b) was increased, if an increase was carried out in step (b). Alternatively, if the vacuum was lowered in step (b), the vacuum in step (d) is preferably increased to a value that is higher than the value that prevailed before step (b). In absolute figures, the second differential value is preferably between 5 and 20 mbar, particularly preferably between 8 and 12 mbar, and is in particular approximately 10 mbar.

The first waiting period is preferably between 20 minutes and 3 hours, particularly preferably between 40 minutes and 1.5 hours, and can in particular be approximately 1 hour. The second waiting period is preferably longer than the first waiting period, preferably longer than the first waiting period by a factor of between 2 and 5, and can in particular be longer than the first waiting period by a factor of approximately 3. The second waiting period is preferably between 1 hour and 6 hours, particularly preferably between 2 hours and 4 hours, and can in particular be approximately 3 hours.

The stated pressure differences and waiting periods are chosen such that an adjustment takes place several times a day and such that, within a defined observation period (e.g. within one shift of the nursing staff), a change in the size of the air fistula is probable on account of the changed pressure conditions.

It is not necessary for the first and/or second waiting periods to be fixed, and instead they can, if appropriate, also be adapted dynamically. For example, the first waiting period in particular can be shortened if, after the increase in the vacuum value, the parameter for the fistula size increases above a predetermined alarm value. In this case, immediate reduction of the vacuum is indicated. The control unit can correspondingly be configured to monitor such an alarm value and, if appropriate, additionally output an alarm signal if the alarm value is exceeded.

The appliance preferably has further features of the kind that are generally customary in thoracic drainage systems, in particular a secretion collection container through which the air aspirated by the suction device is passed in order to separate off liquid and solid bodily secretions. Moreover, a surge tank can be provided in the usual way in order to avoid a return flow of air into the pleural space. The appliance will generally have at least a first tube connection for attachment of a suction tube or suction catheter. Moreover, the appliance can have a second tube connection for attachment of an auxiliary tube or auxiliary catheter. The suction tube and the auxiliary tube are connected to each other, at least at their ends near the patient (the proximal ends), and the lumina delimited by the tubes communicate with each other. In particular, the pressure gauge can be connected to the second tube connection, such that the pressure measurement takes place via the auxiliary tube in an area near the patient, i.e. near the pleural space, without being distorted by the stream of aspirated air and bodily secretions.

According to a further aspect, the present invention makes available a method for thoracic drainage in a patient with an air fistula, said method having the following steps:
  generating a vacuum in the pleural space by means of a suction device;
  determining a size parameter for the air fistula; and
  automatically regulating, in particular with computer control, the vacuum generated by the suction device as a function of this size parameter.

The present invention additionally makes available a method for thoracic drainage in which a vacuum is applied to the pleural space of a patient with an air fistula, which method has the abovementioned steps (a)-(e). This method can be carried out manually, e.g. by a physician or by nursing staff. However, the method is preferably at least partially carried out automatically, i.e. at least the steps (a)-(d) are carried out automatically by a control device, in particular with computer control.

The present invention also makes available a method for thoracic drainage in patients with an air fistula, in which method a size parameter for the air fistula is determined as follows:
  determining a measured value for the vacuum generated in the pleural space;
  determining a measured value for the volumetric flow through the air fistula; and
  calculating the size parameter for the air fistula from the measured values for the volumetric flow and the vacuum.

The size parameter that is determined in this way can be stored or output and/or used to regulate the vacuum.

The present invention further relates to a computer program with code for controlling an appliance for thoracic drainage in patients with an air fistula, said appliance comprising a suction device for generating a vacuum and a digital control device for controlling the suction device, wherein the code, when executed in the digital control device, causes the control device to carry out one of the abovementioned methods.

The computer program can in particular be present in the form of a computer program product on a suitable data carrier, e.g. on a CD-ROM, on a flash memory, etc., or can be made available for download via a network. It can be present in any desired form, e.g. as source code, object code or machine code.

Otherwise, as regards the method and the computer program, the same considerations as for the appliance also apply analogously, in particular as regards the determination and calculation of the size parameter for the air fistula and the considerations to the values of the first and second pressure difference and to the waiting periods. The method can also be carried out using other means than the appliance described above.

BRIEF DESCRIPTION OF THE DRAWINGS

Preferred embodiments of the invention are described below with reference to the drawings, which serve only for explanatory purposes and are not to be interpreted as limiting the invention. In the drawings.

DESCRIPTION OF PREFERRED EMBODIMENTS

Figure 1:
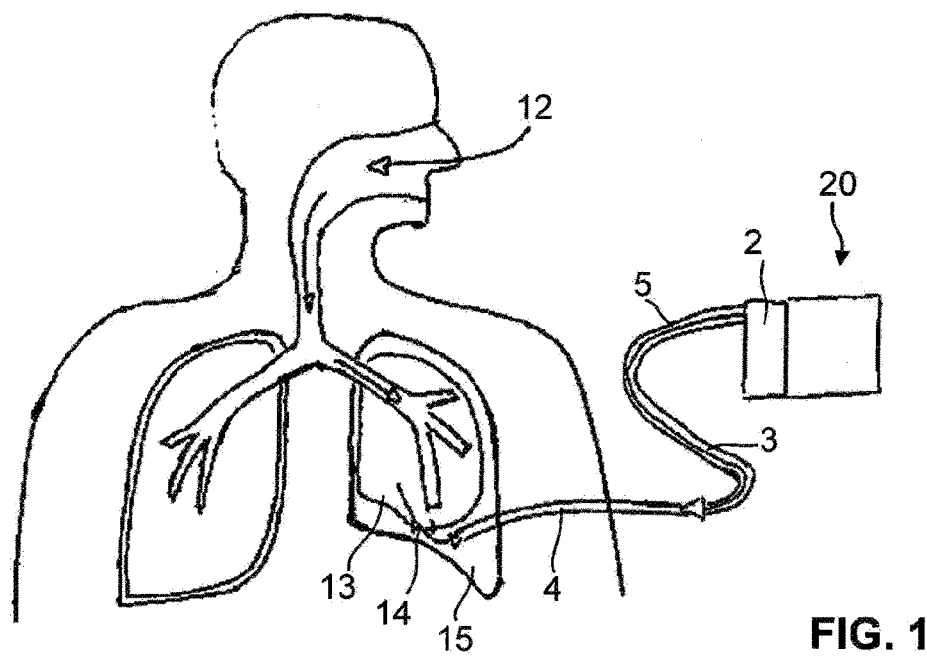
FIG. 1 shows a schematic diagram of thoracic drainage.

FIG. 1 illustrates schematically the principle of thoracic drainage. A patient has an air fistula 14 between a pulmonary lobe 13 and the pleural space 15, which air fistula 14 may have occurred spontaneously or through injury or may be iatrogenic. Air passes through the air fistula from the lung into the pleural space 15. In order to aspirate the air, a catheter 4 extends into the pleural space. This catheter 4 is connected via a tube system, with suction tube 3 and auxiliary tube 5, to a suction appliance 20 with an exchangeable collecting container 2. The collecting container serves to separate bodily secretions that reach the suction appliance 20 along with the aspirated air.

Figure 2:
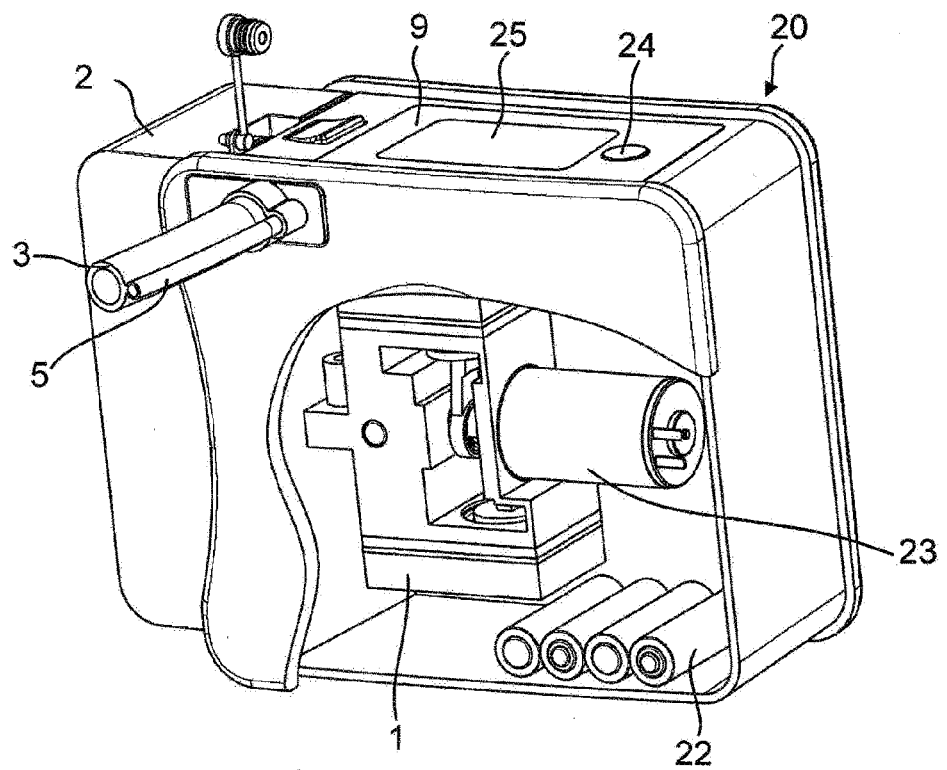
FIG. 2 shows an example of a suction appliance, of which the housing is shown partly in section in order to provide a view of the interior of the housing.

An example of a suitable suction appliance known per se is illustrated in FIG. 2. The suction appliance 20 has a suction pump 1, which is driven by an electric motor 23. The electric motor 23 is controlled by a control device 9. The control device 9 has operating and display elements in the form of a main switch 24 and of a touchscreen display 25. The control device and the electric motor are supplied with power from an energy store in the form of rechargeable batteries 22, such that the suction appliance is self-contained and portable. The suction appliance in FIG. 2 is described in detail in WO 2007/128156, of which the entire content is incorporated by reference into the present description. A suction appliance of generally similar design is commercially available under the name Medela THOPAZ™.

Figure 3:
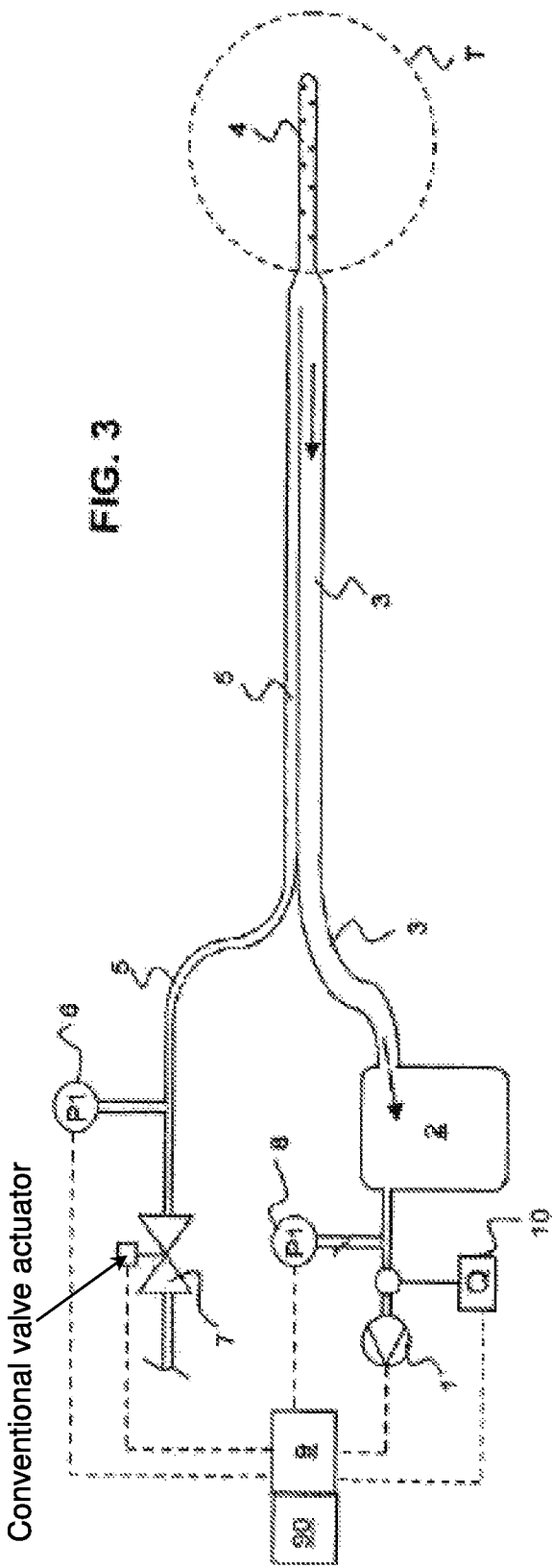
FIG. 3 shows a schematic diagram illustrating the mode of operation of the suction appliance from FIG. 2.

The mode of operation of such a suction appliance is illustrated schematically in FIG. 3. The catheter 4 is located with its proximal end in the pleural space T. The catheter is connected to the proximal end of the suction tube 3 and of the auxiliary tube 5. At its distal end, the suction tube 3 opens into the collecting container 2. The latter is connected to the suction pump 1 in order to generate a vacuum in the collecting container 2. A first pressure gauge 8 and a flow meter 10 are connected between the collecting container 2 and the suction pump 1 and measure the pressure in the collecting container 2 and the volumetric gas flow through the collecting container 2. The distal end of the auxiliary tube is connected to a controllable valve 7 and to a second pressure gauge 6. When the valve 7 is closed, no gas flows through the auxiliary tube 5, and the pressure gauge 6 therefore substantially measures the pressure at the proximal end of the auxiliary tube 5. This pressure corresponds substantially to the pressure in the pleural space T. The control device 9 receives signals from the pressure gauges 6, 8 and from the flow meter 10 and controls the suction pump 1 and the valve 7. For further features of the suction appliance in FIG. 3, reference is made to WO 2005/061025, of which the entire content is herewith incorporated by reference into the present description.

Figure 4:
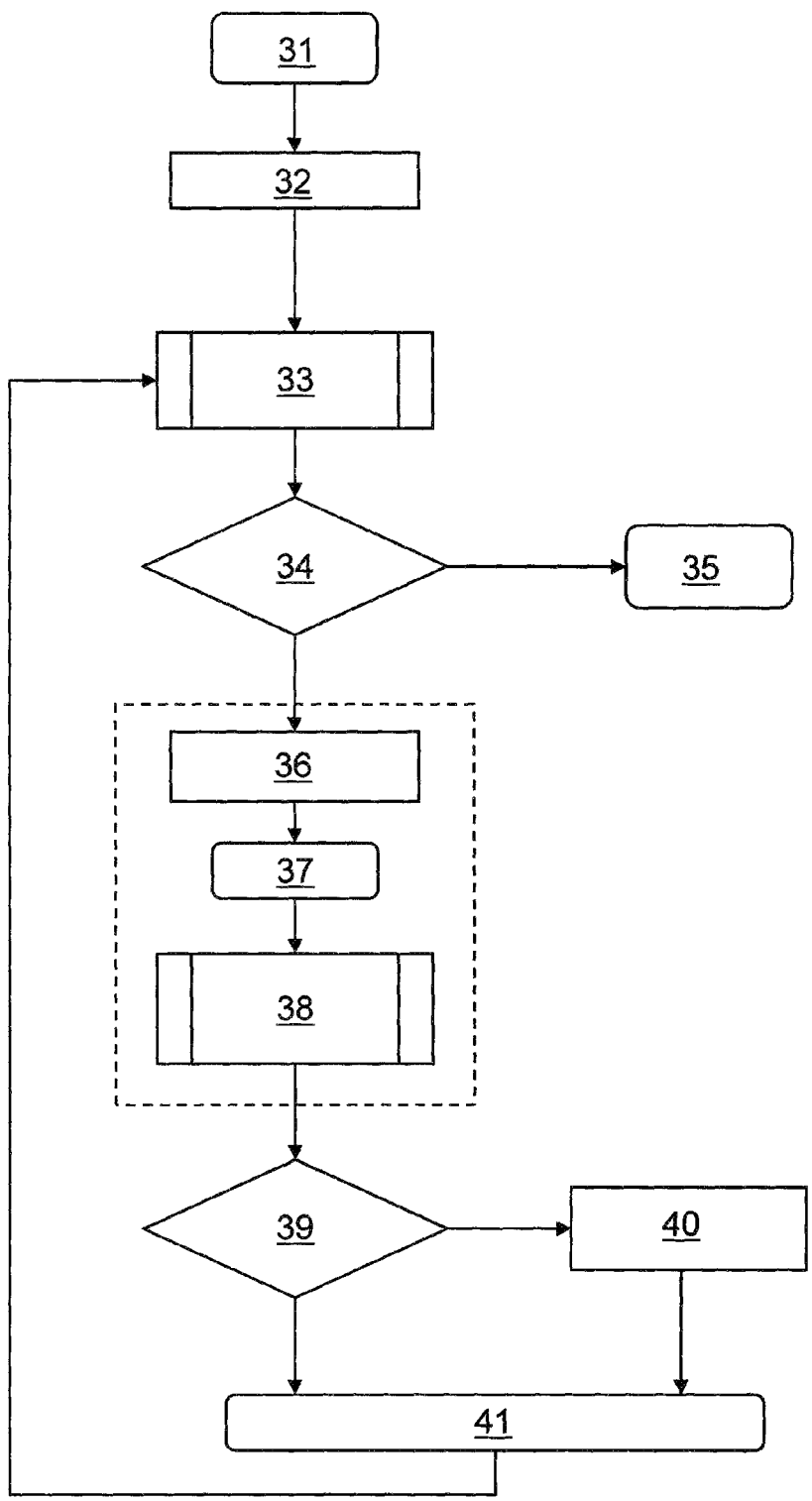
FIG. 4 shows a flow chart for a method according to the invention.

In a preferred embodiment, the control device 9 is a digital control device, i.e. this device comprises a digital processor and, interacting with the latter, a memory 90 in which a computer program is loaded for execution by the processor. When the program is executed, the control device 9 carries out the adaptive algorithm illustrated in FIG. 4 and explained step by step below.

Step 31: Start. In this step, the suction appliance 20 is started up and an initial vacuum is set.

Step 32: Documentation of initial vacuum. The initial vacuum is provided with a time stamp and stored in the memory 90 of the control device 9 for documentation purposes.

Step 33: Determination of a first value of the fistula size. The control device 9 determines a first value of a parameter indicating the size of the air fistula. For this purpose, the control device, using the second pressure gauge 6, measures the value of the vacuum present in the pleural space and, using the flow meter 10, measures the volumetric flow passing through the suction tube 3 from the pleural space. From this, the control device determines a size parameter for the fistula according to the following equation:

$$F = c \log_n \left( \frac{Q}{\sqrt{p}} \right),$$

where
F is the size parameter for the air fistula,
Q is the measured value for the volumetric flow (expressed in millilitres per minute),
p is the measured value for the vacuum (expressed in mbar),
c=1 and n=5.

The result is generally a number between 0 and 5. This number is provided with a time stamp and stored in the memory 90 of the control device, likewise the values Q and p.

Step 34: Test of the fistula size. The size parameter is compared with a predetermined reference value (which can in particular be equal to 1).

Step 35: End. If the size parameter is smaller than or equal to the reference value, a corresponding end signal is output that tells the patient or the medical personnel that the air fistula is practically closed and the thoracic drainage can be expected to be completed.

Step 36: Vacuum increased by a first differential value. If the size parameter exceeds the reference value, the control device 9 increases the pump output such that the vacuum increases by 5 mbar. The new vacuum value is stored with time stamp in the memory 90.

Step 37: First waiting period. In this period (e.g. one hour), the new vacuum value is maintained. The air fistula has the chance to react to the new vacuum value.

Step 38: Determination of the second value of the fistula size. This step proceeds exactly like step 33.

Step 39: Comparison of fistula sizes before and after: The first and second values of the size parameter are read out from the memory 90 and compared with each other. If the second value is greater than the first value, a branch is made after step 40, otherwise after step 41.

Step 40: Vacuum lowered by a second differential value. If the second value is greater than the first value of the fistula parameter, the control device reduces the output of the suction pump until the vacuum has dropped by 10 mbar. Otherwise, the previous vacuum is maintained. The new vacuum value is stored with time stamp in the memory 90.

Step 41: Second waiting period. In this period (3 hours), the vacuum is once again maintained.

Steps 33, 34, 36-39 and 41 and, if appropriate, step 40 are now repeated in the same way until the method ends at step 35. The stored values for the vacuum, the volumetric flow and the size parameter can be read out at any time via an interface or shown on the display.

Compared to the customary clinical practice to date, the frequent adjustments of the vacuum mean that the healing process can be better monitored and ideally sped up.

EXAMPLE 1

Closing Fistula

In a patient 1 with an air fistula, the thoracic drainage system THOPAZ™ was used. A vacuum of 10 mbar was initially set. This resulted in a volumetric flow of 100 ml/min. From this, a fistula size F=2.15 was calculated using the above equation (see step 33). The vacuum was then increased by 5 mbar to 15 mbar. After one hour, the volumetric flow was measured again. This was now 120 ml/min. From this, a fistula size F=2.13 was calculated. The fistula had therefore functionally decreased in size. The vacuum of 15 mbar was therefore maintained for a further 3 hours.

EXAMPLE 2

Opening Fistula

In a patient 2, an initial vacuum of 10 mbar was likewise set. In this patient also, this resulted in a volumetric flow of 100 ml/min, from which a fistula size F=2.15 was calculated. The vacuum was again increased by 5 mbar to 15 mbar, and the volumetric flow was measured after one hour. This was now 240 ml/min, corresponding to a fistula size F=2.56. The vacuum was therefore lowered by 10 mbar to just 5 mbar, and this value was maintained for a further 3 hours.

It is clear that many modifications can be made to the appliances and methods that have been described above by way of example. Thus, the suction device can be any other kind of suction device than the electrical suction pump in FIG. 2, e.g. an attachment for a central hospital vacuum system, as long as the vacuum level can be adjusted by a suitable pressure control. Accordingly, the thoracic drainage system can also be of a completely different construction than that shown in FIGS. 2 and 3. A great many such systems are known from the prior art.

The adaptive algorithm can also be modified or supplemented in many different ways. In particular, the differential values of the vacuum and the waiting periods chosen can also be different, e.g. dynamically adapted to measured values. Moreover, in addition to the fistula size, other parameters, e.g. the amount of liquid secretion, can also be measured automatically and used to automatically regulate the vacuum.

It is possible in principle for steps 31-41 to be carried out completely manually, although an automated procedure is preferred.

What is claimed is:

1. An appliance for thoracic drainage in patients with an air fistula, said appliance comprising:
    a suction device with a suction pump and an electric motor for driving the suction pump, in order to generate a vacuum in the pleural space of a patient;
    a control device for controlling the electric motor of the suction device; and
    at least one measuring device being connected to the control device and comprising at least one of a pressure gauge for measuring the generated vacuum or a flow meter for measuring a volumetric flow,
    wherein the control device is configured to determine a size parameter indicating the functional size of the air fistula by using signals received from at least one of the pressure gauge or the flow meter,
    wherein the control device is configured to control the electric motor such that the level of the vacuum generated by the suction pump is automatically regulated as a function of said size parameter;
    and wherein the control device is configured to carry out a method having the following steps:
    (a) determining a first value of the size parameter;
    (b) changing the output of the suction pump such that the generated vacuum is changed by a first differential value and in such a way that a vacuum is still generated by the suction device in the pleural space, but with a different negative pressure difference in relation to atmospheric pressure;
    (c) determining a second value of the size parameter after a first waiting period;
    (d) changing the output of the suction pump such that the generated vacuum is changed by a second differential value, which has an opposite sign and a greater absolute value compared to the first differential value, if the second value of the size parameter is greater than the first value of the size parameter; and
    (e) repeating steps (a)-(d) after a second waiting period.

2. The appliance according to claim 1, wherein the first differential value has an absolute value of between 2 and 10 mbar.

3. The appliance according to claim 1, wherein the second differential value has an absolute value of between 5 and 20 mbar.

4. The appliance according to claim 1, wherein the first waiting period is between 20 minutes and 3 hours.

5. The appliance according to claim 1, wherein the second waiting period is longer than the first waiting period.

6. The appliance according to claim 1, wherein the second waiting period is between 1 hour and 6 hours.

7. The appliance according to claim 1, wherein the first differential value has an absolute value of between 4 and 6 mbar.

8. The appliance according to claim 1, wherein the second differential value has an absolute value that is greater than the absolute value of the first differential value by a factor of between 1.5 and 3.

9. The appliance according to claim 1, wherein the second differential value has an absolute value of between 8 and 12 mbar.

10. The appliance according to claim 1, wherein the first waiting period is between 40 minutes and 1.5 hours.

11. The appliance according to claim 1, wherein the second waiting period is longer than the first waiting period by a factor of between 2 and 5.

12. The appliance according to claim 1, wherein the second waiting period is between 2 hours and 4 hours.

13. A method for thoracic drainage in a patient with an air fistula, said method comprising the following steps:
    generating a vacuum in the pleural space of the patient by means of a suction device having a suction pump and an electric motor for driving the suction pump;
    determining a size parameter indicating the functional size of the air fistula; and
    automatically controlling the electric motor by means of a control device, such that the level of the vacuum generated by the suction pump is regulated as a function of said size parameter by carrying out the following steps:
    (a) determining a first value of the size parameter for the air fistula based on a pressure measurement of the generated vacuum, the pressure measurement performed by means of a pressure gauge connected to the control device, and/or on a measurement of a volumetric flow, the measurement of volumetric flow being performed by means of a flow meter;
    (b) changing the output of the suction pump such that the generated vacuum is changed by a first differential value and in such a way that a vacuum is still generated by the suction device in the pleural space, but with a different negative pressure difference in relation to atmospheric pressure;
    (c) determining a second value of the size parameter after a first waiting period based on at least one of a pressure measurement of the generated vacuum or a measurement of a volumetric flow;
    (d) changing the output of the suction pump such that the generated vacuum is changed by a second differential value, which has an opposite sign and a greater absolute value compared to the first differential value, if the second value for the size parameter is greater than the first value for the size parameter; and
    (e) repeating steps (a)-(d) after a second waiting period.

* * * * *